United States Patent [19]

Suzuki

[11] Patent Number: 4,544,498

[45] Date of Patent: Oct. 1, 1985

[54] PEARLESCENT LIQUID SUSPENSION

[75] Inventor: Toshio Suzuki, Ichikawa, Japan

[73] Assignee: Kao Corporation, Tokyo, Japan

[21] Appl. No.: 625,299

[22] Filed: Jun. 27, 1984

[30] Foreign Application Priority Data

Jul. 5, 1983 [JP] Japan .................................. 58-120990

[51] Int. Cl.⁴ .............................................. B01J 13/00
[52] U.S. Cl. .............................. 252/547; 252/DIG. 2; 252/DIG. 14
[58] Field of Search ......... 252/547, DIG. 2, DIG. 14

[56] References Cited

U.S. PATENT DOCUMENTS 4,363,755 12/1982 Uchino et al. ....................... 252/545
4,486,334 12/1984 Horiuchi et al. ..................... 252/312

OTHER PUBLICATIONS

Hunting Cosmetics and Toiletries, vol. 96 (1981), pp. 65–78.
Kajl et al., Chemical Abstracts, 89 (1978) #45372.

Primary Examiner—Arthur P. Demers
Attorney, Agent, or Firm—Oblon, Fisher, Spivak, McClelland & Maier

[57] ABSTRACT

A pearlescent liquid suspension comprises essentially (A) a cationic surface active agent, (B) a higher alcohol, and (C) an alpha-mono(methyl-branched alkyl) glyceryl ether. The total amount of these ingredients should be from 1 to 40 wt %, mixing ratios of (A), (B) and (C) lying within an area surrounded by lines connecting the specified points a, b and c on the triangular coordinate of the ternary system.

The suspension according to the invention is more inexpensive than known pearling agents. Further, since it includes crystals which are as fine as 1 to 10 microns, the suspension is more stable and the appearance is more beautiful than known agents.

The pearlescent liquid suspension according to the invention may be added to liquid or paste compositions such as liquid detergent compositions and rinse compositions to give them beautiful pearl luster.

6 Claims, 1 Drawing Figure

FIGURE
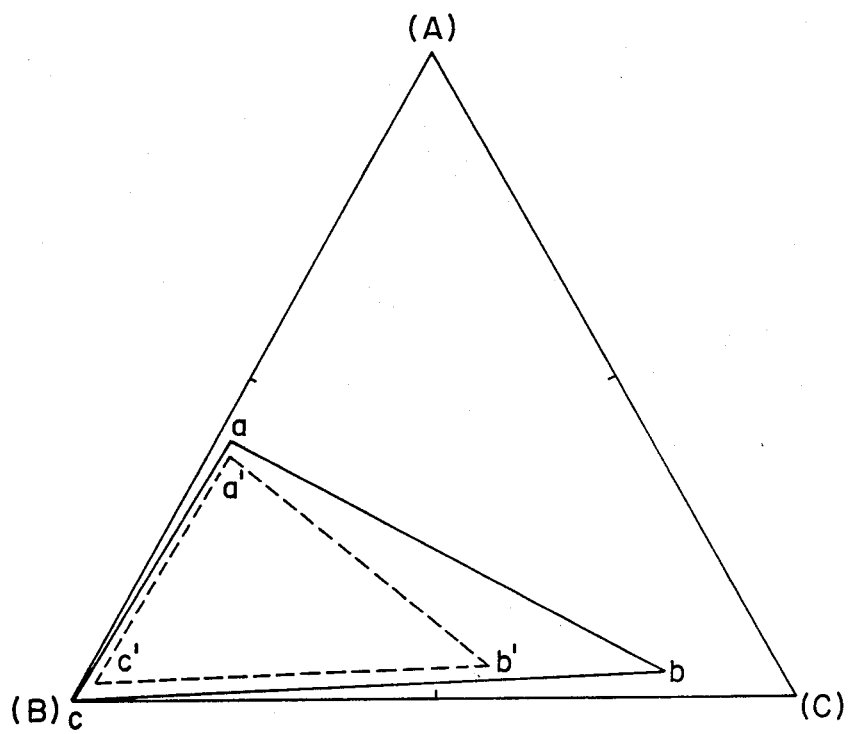

PEARLESCENT LIQUID SUSPENSION

BACKGROUND OF THE INVENTION (i) Field of the Invention

This invention relates to pearlescent liquid suspensions and more particularly, to pearlescent liquid suspensions which comprise cationic surface active agents, higher alcohols, and alpha-mono(methyl-branched alkyl) glyceryl ethers and, if necessary, water-soluble polymer compounds, from which there are produced pearly crystals which are uniform in crystal form and have good high and low temperature stability.

(ii) Description of the Prior Art

In order to enhance the commercial value of cosmetics such as shampoos, rinses, lotions and the like, it is the general practice that these compositions are imparted with beautiful pearl luster appearance. Pearlescent liquid suspension have been prepared by several techniques including, for example, a technique in which there are used powdered products of natural or inorganic materials such as, for example, mica, fish scale, bismuth oxychloride and the like, and a technique of precipitating, in such compositions, crystals of higher fatty acids or salts thereof, ethylene glycol higher fatty acid esters, and the like. Among these techniques, the currently, widely employed technique is a method using ethylene glycol higher fatty acid esters. In this method, the esters which are solid at a normal temperature are added at the time of preparation of shampoo or the like and melted under heating conditions, followed by cooling to produce crystals of the ester. Thus, the liquid is imparted with a pearly appearance. A number of so-called pearling agents capable of producing pearly crystals are reported including ethylene glycol difatty acid esters (Japanese Laid-open patent application Nos. 57-51799, 57-156409, 57-156410, and 57-165308), polyethylene dicarboxylic acid esters (Japanese Laid-open patent application No. 57-67510), ethylene glycol or triethylene glycol fatty acid diesters (Japanese Laid-open patent application No. 56-133400), and polyalkylene glycol difatty acid esters (Japanese Laid-open patent application No. 57-48335).

SUMMARY OF THE INVENTION

In view of the above circumstances, we have made intensive studies of pearling agents which are more inexpensive than known pearling agents and are uniform in size and which are able to stably produce a pearl luster of beautiful appearance in a dispersion of an active agent. As a result, it has been found that mixtures of cationic surface active agents, higher alcohols, and alpha-mono(methyl-branched alkyl) glyceryl ethers in predetermined mixing ratios with or without addition of water-soluble polymers are suitable for the purpose of the invention.

According to the present invention, there is provided a pearlescent liquid suspension which comprises, as essential ingredients, (A) a cationic surface active agent, (B) a higher alcohol, and (C) an alpha-mono(methyl-branched alkyl) glyceryl ether, the total amount of these ingredients being from 1 to 40 wt %, mixing ratios of (A), (B) and (C) lying within an area surrounded by lines obtained by connecting the following points a, b and c on the triangular coordinate of the ternary composition diagram of the sole FIGURE attached herewith a [(A)=40.0, (B)=58.0, (C)=2.0]

b [(A)=4.0, (B)=16.0, (C)=80.0]

c [(A)=0.2, (B)=99.7, (C)=0.1]

Further, the suspension may further comprise 0.1 to 5 wt % of (D) a water-soluble polymer compound.

BRIEF DESCRIPTION OF THE DRAWING

A sole FIGURE is a triangular coordinate of mixing ratios of ingredients (A), (B) and (C) of a pearlescent liquid suspension of the present invention, in which (A) represents a cationic surface active agent, (b) represents a higher alcohol, and (C) represents an alpha-mono(methyl-branched alkyl) glyceryl alcohol.

DETAILED DESCRIPTION OF THE INVENTION AND PREFERRED EMBODIMENTS

The cationic surface active agents which are ingredient (A) of the invention are not limited to any specific ones and may be those agents which are ordinarily employed in hair rinses. Preferably, quaternary ammonium salts of the following formula (I) are used:

in which one or two of $R_1$, $R_2$, $R_3$ and $R_4$ independently represent a linear or branched alkyl or hydroxyalkyl group having from 8 to 22 carbon atoms, and the others independently represent an alkyl group or hydroxyalkyl group having from 1 to 3 carbon atoms, a benzyl group, or a polyoxyethylene group in which the total number of moles added is not higher than 10, and X represents a halogen atom or an alkylsulfate having from 1 to 2 carbon atoms. Specific examples of the quaternary ammonium salts include distearyldimethylammonium chloride, stearyltrimethylammonium methosulfate, stearyltrimethylammonium chloride, stearyldimethylbenzylammonium chloride, docosyltrimethylammonium methosulfate, docosyltrimethylammonium chloride, docosyldimethylbenzylammonium chloride, didocosyldimethylammonium chloride, lauryldiethylbenzylammonium chloride, lauryltrimethylammonium bromide, distearylmethylhydroxymethyl chloride, cetyltrimethylammonium chloride, N-stearyl-N,N,N-tri(polyoxyethylene) ammonium chloride (3 moles added in total), cetyltriethylammonium bromide, stearyldimethylammonium chloride, and the like.

These ingredients (A) are used, singly or in combination, in an amount of 0.05 to 20 wt % (hereinafter referred to simply as %), preferably from 0.1 to 10 wt %, of the pearlescent liquid suspension. Amounts less than 0.05% result in a phase separation, whereas amounts exceeding 20% lead to a loss of pearl luster.

The higher alcohols which are ingredient (B) of the invention are alcohols having a linear or branched alkyl or alkenyl group containing from 12 to 26 carbon atoms. Preferable examples of the alcohols include stearyl alcohol, behenyl alcohol, cetyl alcohol, cetostearyl alcohol (mixture of cetyl alcohol and stearyl alcohol), and the like. The ingredient (B) is generally used in an amount of from 0.2 to 29%, preferably from 0.5 to 25%.

The alpha-mono(methyl-branched alkyl) glyceryl ethers of ingredient (C) are preferably represented by the following general formula (II), $$R_5-OCH_2CH(OH)CH_2OH \quad (II)$$

in which $R_5$ represents a methyl-branched saturated hydrocarbon having from 12 to 24 carbon atoms. These ethers are prepared according to the process described, for example, in Japanese Laid-open patent application No. 56-39033. More preferably, $R_5$ in the formula (II) is a group of the following formula (III), $$CH_3-(CH_2)_m-\underset{\underset{CH_3}{|}}{CH}-(CH_2)_n- \quad (III)$$

in which m is an integer from 2 to 13, n is an integer from 3 to 22, and the sum of m and n is from 9 to 21. Most preferably, the sum of m and n in the formula (III) is from 11 to 17 (i.e. the total number of carbon atoms in the alkyl group ranging from 14 to 20), and is particularly 15 (i.e. the total number of carbon atoms in the alkyl group is 18). Preferably, the branched methyl group is positioned near at the center of the main alkyl chain.

Physical properties of typical alpha-mono(methyl-branched alkyl) glyceryl ethers are shown below.

| Methyl-branched Alkyl Group | Melting Point | Specific Gravity (30° C.) | Viscosity (30° C.) |
|---|---|---|---|
| Methyl-branched Stearyl [made predominantly of the group of formula (III), wherein m = 7 and n = 8] | 23° C. | 0.912 | 856 |

These ethers of ingredient (C) are used in amounts of from 0.01 to 40%, preferably 0.05 to 20%, of the pearlescent liquid suspension.

The water-soluble polymers of ingredient (D) are cellulose derivatives, polyvinylpyrrolidone, methoxyethylene-maleic anhydride copolymers, and the like. Of these, there are preferably used cellulose derivatives of the following formula (IV)

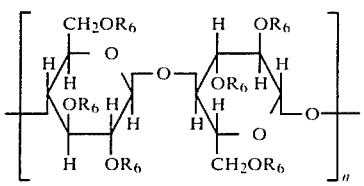

(IV)

in which $R_6$s independently represent a hydrogen atom, a group $-CH_2OH$, a group $-(CH_2CH_2O)_m-$ wherein m is an integer from 1 to 5, a $CH_3$ group, a $C_2H_5$ group, or a $-C_3H_6OH$, and n is an integer from 5 to 5,000. Specific examples of these preferable derivatives include hydroxyethyl cellulose, and hydroxymethyl cellulose.

These ingredients (D) do not show any satisfactory effect when used in amounts not larger than 0.1% and any further effects cannot be expected when they are used in excess of 5%. Thus, the amount of the ingredient (D) is from 0.1 to 5%.

The pearlescent liquid suspension of the invention should essentially comprise the ingredients (A), (B) and (C), and the total amount of these ingredients ranges from 1 to 40%, preferably from 2 to 30%. The mixing ratios of the ingredients (A), (B) and (C) should lie within an area surrounded by straight lines connecting the afore-indicated points (a, b, c) on the triangular coordinate of the ternary system. Preferably, the mixing ratios of (A), (B) and (C) lie within an area surrounded by the following three points (a', b', c')

a' [(A)=38.0, (B)=59.0, (C)=3.0]

b' [(A)=5.0, (B)=40.0, (C)=55.0]

c' [(A)=3.0, (b)=95.0, (C)=2.0]

The pearlescent liquid suspension of the invention is obtained by heating a solution containing the above ingredients to give a uniform solution, and forcibly or naturally cooling the solution thereby crystallizing the ingredients.

In the practice of the invention, in order to facilitate the crystallization, known crystallizing agents may be added, if necessary. Examples of the crystallizing agents include water-soluble inorganic or organic salts such as ammonium chloride, sodium sulfate, sodium citrate, sodium succinate, sodium oxalate and the like, citric acid, succinic acid, oxalic acid, urea, and the like. These agents may be used singly or in combination and are preferably used in an amount of from 0.1 to 5%.

In the preparation of the pearlescent liquid suspension according to the invention, the agitation speed is not critical and is generally in the range as low as about 10 to 100 r.p.m. If used, the crystallizing agent and the water-soluble polymer compound of ingredient (D) should preferably be dissolved in a dispersing medium prior to use. In order to cause the pearl crystallization to quickly proceed, the temperature of the solution should preferably be lowered to a level from a normal temperature to 40° C. The manner of cooling may not be critically limited and either slow or rapid cooling may be used.

When thus cooled, the solution entirely assumes beautiful pearl luster. If necessary, the pearlescent liquid suspension may further comprise pH adjusters, preservatives, colorants, perfumes, UV absorbers and the like.

The thus obtained pearlescent liquid suspension of the invention can be added to liquid compositions such as liquid detergent compositions, liquid or paste rinses in amounts which may vary depending on the purpose, by which beautiful pearl luster can be imparted to these compositions. The amount of the dispersion, for example, in liquid composition is in the range of from 1 to 20%, preferably 2 to 10%.

The pearlescent liquid suspension includes thereon crystals which are as fine as about 1 to 10 microns and are thus more uniform and have more beautiful appearance than known molten pearlescent liquid suspensions which have particles having sizes over about 30 microns.

The present invention is particularly described by way of examples, which should not be construed as limiting the present invention thereto. Test methods used in examples are as follows.

(1) Appearance

A sample is placed in a transparent glass container with a volume of 100 ml and a pearl luster appearance was visually observed. It will be noted that if bubbles or foams were contained in sample, the sample was subjected to a centrifugal separator for defoaming.

O = Uniform in pearl luster
X = Turbid, emulsified or nonuniform in pearl luster

(2) High Temperature Stability

A sample was placed in a transparent glass container, hermetically sealed, and was kept in a thermostat of 50° C. for one month, followed by visually observing to determine presence or absence of phase separation or coagulation of the sample.

O = Singularities such as separation, coagulation of pearl luster, and loss of gloss were not recognized.
X = Singularities such as separation, coagulation of pearl luster, and loss of gloss were recognized.

(3) Low Temperature Stability

A sample was placed in a transparent glass container, hermetically sealed, and kept in a thermostat of −5° C. for one month, followed by visually observing to determine presence or absence of phase separation or solidification of the sample.

O = Fluidity without involving separation and solidification was recognized.
X = Singularities such as separation, solidification and the like were recognized.

EXAMPLE 1

| | |
|---|---|
| (1) Monostearyltrimethylammonium chloride | 1.0 (%) |
| (2) Behenyl alcohol | 2.0 |
| (3) Alpha-mono(isostearyl) glyceryl ether (in formula (III), m = 7 and n = 8) | 0.4 |
| (4) Propylene glycol | 1.0 |
| (5) Hydroxyethyl cellulose | 0.6 |
| (6) Water | 95.0 |

To (5) and (6) heated to 80° C. was added a mixture of (1) to (4) heated to and melted at the same temperatures as indicated above, followed by cooling while agitating. The resulting composition showed a pearly appearance with good storing stability.

EXAMPLE 2

| | |
|---|---|
| (1) Distearyldimethylammonium chloride | 0.6 (%) |
| (2) Monostearyltrimethylammonium chloride | 0.4 |
| (3) Cetyl alcohol | 2.0 |
| (4) Alpha-mono(isostearyl) glyceryl ether [in formula (III), m = 7 and n = 8] | 1.0 |
| (5) Propylene glycol | 1.0 |
| (6) Hydroxyethyl cellulose | 0.6 |
| (7) Water | 94.4 |

To (6) and (7) heated to 80° C. was added a mixture of (1) to (5) heated to and melted at the same temperature as indicated above, followed by cooling under agitation. The composition showed a pearly appearance and good storing stability.

EXAMPLE 3

To water of 80° C. was added each of mixtures of the respective ingredients, heated to and melted at the same temperature, indicated in table 1, followed by cooling under agitation. The results are shown in Table 1.

TABLE 1

| Composition | 1 | 2 | 3 | 4 | 5 | 6 | 7 | 8 | 9 | 10 | 11 |
|---|---|---|---|---|---|---|---|---|---|---|---|
| Stearyltrimethylammonium chloride | 0.5 | 0.01 | 1.9 | 0.08 | 0.1 | 0.4 | 1 | 4 | 1.2 | 0.3 | 10.5 |
| Behenyl alcohol | 4.5 | 4.85 | 2.5 | 2.55 | 9.8 | 1.6 | 15 | 8 | 10 | 29.4 | 23.4 |
| Alpha-mono(isostearyl) glyceryl ether [in formula (III), m = 7 and n = 8] | 0 | 0.14 | 0.6 | 2.37 | 0.1 | 8 | 4 | 8 | 13.8 | 0.3 | 1.1 |
| Water | 95 | 95 | 95 | 95 | 90 | 90 | 80 | 80 | 75 | 70 | 65 |
| Appearance | X | X | X | X | O | O | O | O | O | O | O |
| High temperature stability | X | X | X | X | O | O | O | O | O | O | O |

As is clear from these results, satisfactory pearlescent liquid suspensions are obtained only when the mixing ratios of the three ingredients (A), (B) and (C) lie within an area surrounded by straight lines connecting the three points of a, b, c of the sole FIGURE.

EXAMPLE 4

Pearlescent liquid suspension having compositions indicated in tables 2-1 and 2-2 were prepared and evaluated in the same manner as in Example 1.

TABLE 2-1

| Composition | 1 | 2 | 3 | 4 | 5 | 6 | 7 | 8 | 9 | 10 |
|---|---|---|---|---|---|---|---|---|---|---|
| Ingredient (A) | | | | | | | | | | |
| Stearyltrimethylammonium chloride | 0.4 | | | 0.4 | 0.4 | 0.4 | | | | |
| Distearyldimethylammonium chloride | | 0.4 | | | | | 0.4 | | 0.4 | |
| Cetyltrimethylammonium chloride | | | 0.4 | | | | | 0.4 | | 0.4 |
| Ingredient (B) | | | | | | | | | | |
| Cetyl alcohol | 1.0 | 1.0 | 1.0 | | | | | | 1.0 | |
| Stearyl alcohol | | | | 1.0 | | | | | | |
| Behenyl alcohol | | | | | 1.0 | 1.0 | 1.0 | 1.0 | | 1.0 |
| Ingredient (C) | | | | | | | | | | |
| Alpha-mono(isostearyl) glyceryl ether [in formula (III), m = 7 and n = 8] | 0.5 | 0.5 | 0.5 | 0.5 | 0.5 | | | | 0.5 | 0.5 |
| Stearyl glyceryl ether | | | | | | 0.5 | 0.5 | 0.5 | | |

TABLE 2-1-continued

| Composition | 1 | 2 | 3 | 4 | 5 | 6 | 7 | 8 | 9 | 10 |
|---|---|---|---|---|---|---|---|---|---|---|
| Ingredient (D) | | | | | | | | | | |
| Hydroxyethyl cellulose | 0.7 | 0.7 | 0.7 | 0.2 | 0.6 | 0.6 | 0.6 | 0.6 | | |
| Hydroxymethyl cellulose | | | | | | | | | 1.0 | 1.0 |
| Water | balance | balance | balance | balance | balance | balance | balance | balance | balance | balance |
| Pearl State | | | | | | | | | | |
| Appearance | O | O | O | O | O | X | X | X | O | O |
| High temperature stability | O | O | O | O | O | X | X | X | O | O |
| Low temperature stability | O | O | O | O | O | X | X | X | O | O |

TABLE 2-2

| Composition | Inventive Product 1 | Reference 1 | Inventive Product 2 | Reference 2 | Reference 3 | Inventive Product 3 | Inventive Product 4 | Inventive Product 5 | Reference 4 |
|---|---|---|---|---|---|---|---|---|---|
| Ingredient (A) | | | | | | | | | |
| Stearyltrimethylammonium chloride | 0.2 | 0.2 | 0.2 | 0.2 | 0.5 | 0.5 | 0.5 | 0.5 | 0.5 |
| Distearyldimethylammonium chloride | 0.8 | 0.8 | 0.8 | 0.8 | — | — | — | — | — |
| Ingredient (B) | | | | | | | | | |
| Cetyl alcohol | 2.0 | 2.0 | — | — | — | — | — | — | — |
| Behenyl alcohol | — | — | 2.0 | 2.0 | 4.0 | 4.0 | 4.0 | 4.0 | 4.0 |
| Ingredient (C) | | | | | | | | | |
| Alpha-mono(isostearyl) glyceryl ether [in formula (III), m = 7 and n = 8] | 1.0 | — | 0.5 | — | 0.01 | 0.1 | 1.0 | 5.0 | 10.0 |
| Ingredient (D) | | | | | | | | | |
| Hydroxyethyl cellulose | 1.0 | 1.0 | 0.4 | 0.4 | 0.6 | 0.6 | 0.6 | 0.6 | 0.6 |
| Pearl State | | | | | | | | | |
| Appearance | O | X | O | X | X | O | O | O | O |
| High temperature stability | O | X | O | X | X | O | O | O | X |
| Low temperature stability | O | X | O | X | X | O | O | O | O |

What is claimed is:

1. A pearlescent liquid suspension comprising as essential ingredients (A) a cationic surface active agent, (B) a higher alcohol, and (C) an alpha-mono(methylbranched alkyl) glyceryl ether, the total amount of these ingredients being from 1 to 40 wt %, mixing ratios of (A), (B) and (C) lying within an area surrounded by lines obtained by connecting the following points a, b and c on the triangular coordinate of the ternary system of the sole FIGURE attached.

a [(A)=40.0, (B)=58.0, (C)=2.0]

b [(A)=4.0, (B)=16.0, (C)=80.0]

c [(A)=0.2, (B)=99.7, (C)=0.1]

2. The pearlescent liquid suspension according to claim 1, wherein said cationic surface active agent is represented by the following general formula (I),

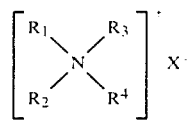

(I)

in which one or two of $R_1$, $R_2$, $R_3$ and $R_4$ independently represent a linear or branched alkyl or hydroxyalkyl group having from 8 to 22 carbon atoms, and the others independently represent an alkyl group or hydroxyalkyl group having from 1 to 3 carbon atoms, a benzyl group, or a polyoxyethylene group in which the total number of moles added is not higher than 10, and X represents a halogen or an alkylsulfate having from 1 to 2 carbon atoms.

3. The pearlescent liquid suspension according to claim 1, wherein said higher alcohol is an alcohol having a linear or branched alkyl or alkenyl group having from 12 to 26 carbon atoms.

4. The pearlescent liquid suspension according to claim 1, wherein said alpha-(methylbranched alkyl) glyceryl ether is represented by the following general formula (II), $$R_5—OCH_2CH(OH)CH_2OH \quad (II)$$

in which $R_5$ represents a methyl-branched saturated hydrocarbon group having from 12 to 24 carbon atoms.

5. The pearlescent liquid suspension according to claim 4, wherein $R_5$ in the formula (III) is a group of the following formula (III),

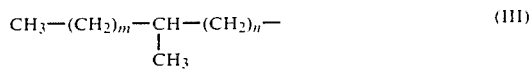

(III)

in which m is an integer from 2 to 14, n is an integer from 3 to 11, and the sum of m and n is from 9 to 21.

6. A pearlescent liquid suspension comprising as essential ingredients (A) a cationic surface active agent, (B) a higher alcohol, (C) an alpha-mono(methylbranched alkyl) glyceryl ether, and (D) a water-soluble polymer compound, the total amount of ingredients (A), (B) and (C) being from 1 to 40 wt %, an amount of ingredient (D) being from 0.1 to 5 wt %, mixing ratios of (A), (B) and (C) lying within an area surrounded by lines obtained by connecting the following points a, b and c on the triangular coordinate of the ternary system of the sole FIGURE attached.

a [(A)=40.0, (B)=58.0, (C)=2.0]
b [(A)=4.0, (B)=16.0, (C)=80.0]
c [(A)=0.2, (B)=99.7, (C)=0.1]

* * * * *